United States Patent [19]

Davis

[11] Patent Number: 4,665,570
[45] Date of Patent: May 19, 1987

[54] FACE MASK SEAL

[76] Inventor: James E. P. Davis, 2210 Wilshire Blvd., Santa Monica, Calif. 90403

[21] Appl. No.: 796,691

[22] Filed: Nov. 12, 1985

[51] Int. Cl.$^4$ .............................................. A42B 1/06
[52] U.S. Cl. ............................................ 2/428; 2/440
[58] Field of Search .................................... 2/428, 440

[56] References Cited

U.S. PATENT DOCUMENTS

| 295,242 | 3/1884 | Genese ..................................... 2/440 |
| 861,504 | 7/1907 | Cover ...................................... 2/440 |
| 1,295,391 | 2/1919 | Troppman .............................. 2/440 |
| 2,393,533 | 1/1946 | Heinz ...................................... 2/440 |
| 3,725,953 | 4/1973 | Johnson et al. ........................ 2/428 |
| 3,789,428 | 2/1974 | Martin et al. ...................... 2/428 X |
| 4,480,429 | 11/1984 | Knox ................................. 2/440 X |

Primary Examiner—Louis K. Rimrodt
Attorney, Agent, or Firm—Roger A. Marrs

[57] ABSTRACT

A conformal seal carried on a face mask is disclosed herein which is mounted about the edge marginal peripheral region of a rigid shell intended to be placed over the nose and mouth areas of a user. The seal includes an endless toroid made with a pliable membrane preferably filled with a deformable filler material so, that upon donning the mask, the seal causes the filler material volume to become smaller in cross section so that its peripheral length is shorter or reduced in cross section as compared with the peripheral length of the toroidal membrane. Thus, the slack membrane allows the filler material to conform to and seal with any irregular face against which it is applied.

10 Claims, 6 Drawing Figures

FACE MASK SEAL

BACKGROUND OF THE INVENTION

1. Field of the Invention

The present invention relates to sealing means for facial masks and, more particularly, to a novel sealing means adapted to conform with a variety of facial irregularities against which the sealing means is forcibly pressed so as to provide an airtight seal against the face.

2. Brief Description of the Prior Art

In the past, it has been the conventional practice in the aircraft, hospital, safety and other fields to provide a variety of breathing masks such as oxygen masks, respirator masks or the like. Each of the respective masks includes means for sealing about the edge of the mask which bears against the face of the user. Some conventional masks include a gas filled expandable tube which surrounds the mouth and nose region of the user and serves as a face sealing mechanism to prevent fluid communication between the interior of the mask and the surrounding environment. Although a variety of conventional masks including sealing means provide a comfortable and reliable seal on users having smooth skin or faces, those users having face grooves or wrinkles cannot be sealed with the conventional gas-filled expandable tube. Problems and difficulties are encountered which stem largely from the fact that as more head strap pressure is applied, the mask and its gas pressure filled expandable tube tightens the skin or membrane of the tube. In so tightening, the membrane of the tube bridges the gaps or irregularities in the surface of the face instead of filling these gaps and irregularities and sealing them against breathing gas leakage.

In particular, conventional gas-filled expandable tubes become taut and less pliable or malleable as head strap forces are increased. The external surface of the tube becomes rigid and hard and effective sealing requires that the hardened tube exert sufficient force against the abutting surface to press out wrinkles and irregularities. Although these prior sealing means are comfortable and seal well on smooth faces, gaps, ridges or irregularities in the face are not occupied by the seal. Extreme head strap forces needed to create a seal are extremely uncomfortable and usually fail to adequately seal the breathing gas.

Therefore, there has been a long standing need to provide a novel sealing means for oxygen or respirator masks which will readily seal against skin surfaces which are deeply wrinkled or present deep irregularities so that breathing gas flow will not leak between the interior of the mask and the surrounding environment.

SUMMARY OF THE INVENTION

Accordingly, the above problems and difficulties are obviated by the present invention which provides a novel sealing means for an oxygen or respirator mask wherein the shell of the mask includes a substantially oval peripheral edge marginal region carrying an endless toroidal tube-like membrane. The membrane is substantially occupied by a filler material and an air relief orifice is operably disposed on the membrane so as to expel air when compression of the membrane and the filler takes place. As pressure to the membrane is increased, air escapes through the orifice and the filler material conforms to the facial irregularities on the surface against which the membrane is pressed.

Accordingly, it is among the primary objects of the present invention to provide a novel facial seal for oxygen or respiratory masks which includes a toroidal tube-like membrane of endless configuration which is highly deformable so as to conform to facial irregularities and thereby providing an effective seal.

Another object of the present invention is to provide a novel facial seal which is highly malleable or pliable so that portions of the toroidal membrane will pack into facial irregularities without excessive head strap force.

Yet another object of the present invention is to provide a novel sealing means having filler material incorporated into a toroidal membrane which is pliable so that upon the placement of force on the mask's head strap, the filler material and the membrane will bear into gaps and facial irregularities. A feature of the invention resides in providing an orifice in the toroidal membrane for exhausting air within the toroidal membrane as force is applied to the mask in order to increase the pliability of the filler and toroidal membrane materials.

Still a further object of the present invention is to provide an effective sealing means for face masks having filler material incorporated into a toroidal endless membrane having an air passageway leading through the membrane whereby pressure applied to the membrane causes the filler material and the membrane to occupy facial irregularities as air is exhausted through the orifice.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

DESCRIPTION OF THE PREFERRED EMBODIMENT

Figure 1:
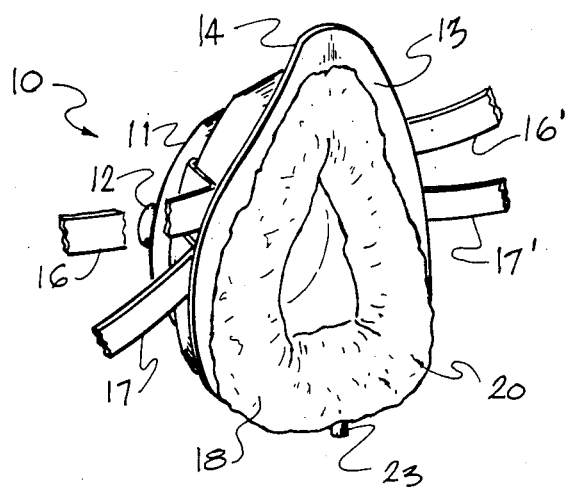
FIG. 1 is a rear perspective view of a facial mask presenting the novel sealing means of the present invention.

Referring to FIG. 1, the novel face seal of the present invention is illustrated in the general direction of arrow 10 which includes a breathing mask 11 coupled to a suitable oxygen supply via a conduit or hose 12. The mask 11 includes a rigid shell 13 having a substantial circular or oval edge marginal region 14. The frame ends of a head strap arrangement comprised of straps 16 and 17 are attached to shell 13 so that as the straps are placed about the head of the user, the mask is drawn into facial contact with the user about his nose and mouth. In order to seal the interior of the mask from the surrounding environment when the mask is worn on the user and to provide comfort for the wearing of the mask, a sealing means 18 is disposed and adhesively carried to the inner surface of the mask shell edge marginal region 14. The sealing means 18 is of a substantially similar configuration as the edge marginal region of the shell and is substantially thick so that the shell does not come into contact with the facial surface of the user.

Figure 2:
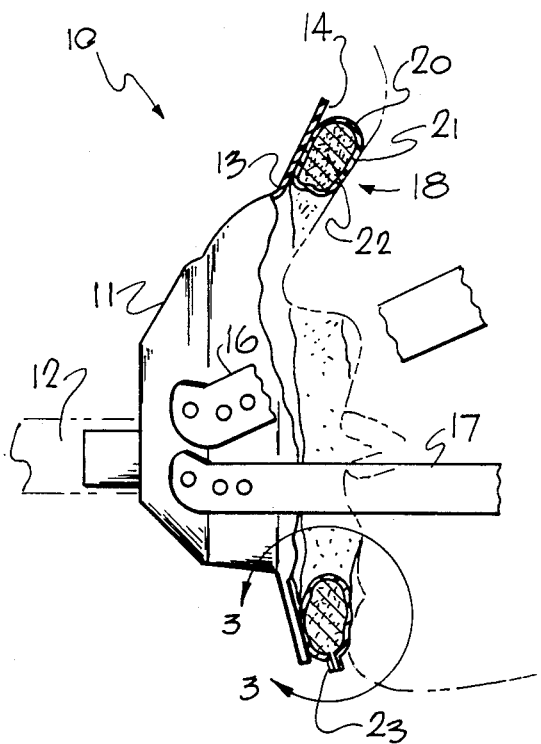
FIG. 2 is an enlarged cross-sectional view of the face mask shown in FIG. 1.

As shown in FIG. 2, the sealing means 18 comprises a toroidal tube 20 which is sometimes referred to as a doughnut comprising an endless casing or membrane 21 which is filled with a fiber-like filler material 22 or the like. The filler material is preferably open-celled and contains the characteristics of being compressible so that its overall volume and surface peripheral length may be shortened. The sealing means 18 is further characterized as being pliable and malleable with the membrane 21 being soft and adapted to be conformal when pressed against a surface having irregularities. A feature of the sealing means resides in the provision of a bleed orifice 23 for expelling or relieving air within the confines of the membrane 21 when the sealing means is pressed against the face of the user. Also, when pressure is relieved from the sealing means, air is permitted to reenter the interior of the membrane 21 as pressure is removed from the sealing means.

Figure 3:
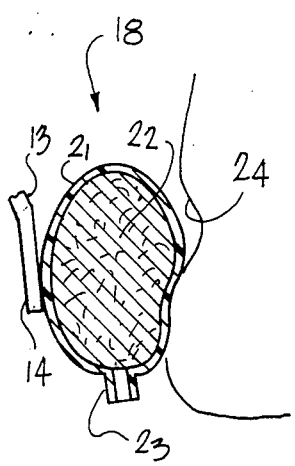
FIG. 3 is an enlarged transverse cross-sectional view of the sealing means shown in FIG. 2 as taken in the direction of arrows 3—3 thereof.
Figure 4:
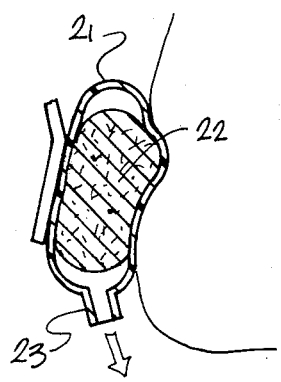
FIG. 4 is a view similar to the view of FIG. 3 showing mask head strap force applied to the sealing means so as to occupy facial irregularities.

Referring now in detail to FIG. 3, an enlarged illustration is shown of the sealing means 18 preparatory for pressing against the facial area of the user. The facial area is illustrated as having an enlarged wrinkle or depression indicated by numeral 24 which cannot be sealed by a conventional rigid inflated seal. The membrane 21 is pliable and the filler material may be of a suitable variety of fibers. The cross-sectional length of the periphery of the filler material and the cross-sectional length of the periphery of the external surface of the membrane 21 are substantially the same. However, as shown in FIG. 4, as the head strap is applied to mount the mask on the face of the user, the compression of the engagement of the sealing means with the facial surface causes the air in the membrane to exhaust or escape through the orifice 23. Thereupon the filler material is packed into the facial irregularity 24 as illustrated. Furthermore, the filler material volume has become smaller so that its peripheral surface is reduced as compared with the peripheral surface of the toroidal membrane 21. This relationship is further shown in FIG. 4 wherein the slack membrane of the sealing means allows the filler material 22 to take whatever shape is necessary to fill and seal the face wrinkle 24. Thus, the sealing means is conformal to the irregularity of the face and the conventional bridging effect by the use of a standard rigid or inflated tube seal is avoided.

Therefore, by first packing the membrane to an even fullness with a springy filler material 22 that will become relatively small in volume under compression, the packing quality of the filler material is used to obtain a superior seal over an irregular surface to which it is applied. When the mask is removed from the face of the user, the springy quality of the filler causes it to expand back to the limits of the internal area of the membrane. Air reenters through the orifice 23 during the release of pressure on the sealing means. When the mask is reapplied to the facial area, it will again perfectly pack all the facial skin irregularities as air bleeds out of the orifice 23.

Figure 5:
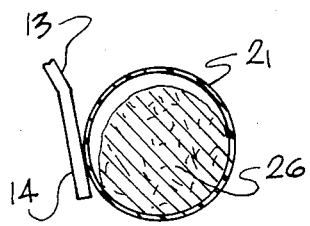
FIG. 5 is a transverse cross-sectional view of another sealing means incorporating the present invention.
Figure 6:
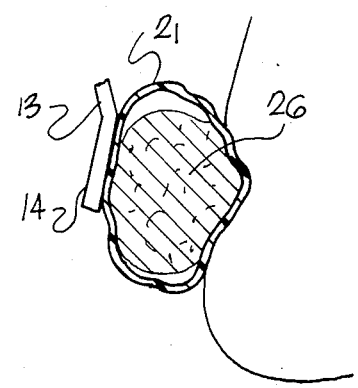
FIG. 6 is a view similar to the view of FIG. 5 showing the alternate version of the invention under head strap force to occupy surface irregularities and gaps.

Referring to FIGS. 5 and 6, another embodiment of the invention is illustrated adapted to obtain a similar packing effect through the employment of an internal filler which does not change in volume when the mask is mounted to the face of the user. In FIG. 5, the toroidal membrane is filled with non-compressible material 26 taking the form of oil, water, clay or powder. Since the membrane peripheral surface is greater than the peripheral surface of the filler material, the slack arrangement is created when the mask is first assembled. No orifice or bleed is implied and the membrane surface is airtight. The clay-like packing 26 is of a quality to deform under applied head strap forces so as to occupy the gap or irregularity in the surface of the skin while the slack membrane of the sealing means contains the filler material.

Therefore, by creating a slack relationship between the skin or external peripheral surface of the membrane of the sealing means and the peripheral surface of the filler material, by either construction shown in FIGS. 3 or 4 or FIGS. 5 and 6, the packing quality of the filler material is allowed to provide a superior face sealing means.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A face mask sealing device for sealing against an irregular facial surface of the user to prevent passage of vapors or gas therebetween, the combination comprising:
    a hollow mask having an edge marginal portion adapted to cover the irregular facial area;
    sealing means carried on said mask edge marginal portion separating said edge marginal region from the facial area; and
    said sealing means having a closed, thin film, toroidal, distortable membrane having a smooth and regular external surface and enclosing a continuous, pliable and deformable filler material adapted under pressure to forcibly urge a porton of said thin film membrane to occupy adjacent surface irregularities of the facial area.

2. The invention as defined in claim 1, wherein:
    said membrane and said filler material are characterized as cooperatively creating a slack relationship between said membrane and the peripheral surface of said filler material to allow said filler material to pack into said facial irregularities.

3. The invention as defined in claim 2 including:
    said filler material being compressible; and
    an air relief orifice carried on said membrane for expelling said air from said closed membrane when under pressure urging said compressible filler material and a portion of said membrane to occupy adjacent surface irregularities of said facial area.

4. The invention as defined in claim 3 wherein:
    said compressible filler material is an open cellular compressible material having a peripheral surface substantially equal to a peripheral surface of said membrane in a first uncompressed condition; and
    said compressible filler material peripheral surface becoming substantially less than said membrane peripheral surface in a second compressed condition so as to create a slack membrane allowing said compressible filler material to conform to the irregular surface of the facial area.

5. The invention as defined in claim 1 wherein:
said filler material is a non-compressible material taken from the group consisting of oil, water, clay or powdered product.

6. The invention as defined in claim 5 wherein:
said membrane includes an outer periphery surface that is of greater cross-section than the cross-section of said non-compressible filler material periphery so as to establish said slack relationship.

7. The invention as defined in claim 6 including:
strap means carried about said membrane for selectively applying pressure to said sealing membrane and said non-compressible filler material.

8. In a sealing means for a face mask deformable under pressure for conforming to surface irregularities comprising:
a toroidal membrane of pliable composition having an external peripheral surface of given cross-section in a pre-pressurized condition;

a compressible filler material enclosed in said membrane having a peripheral surface substantially equal to said membrane given cross-section in said pre-pressurized condition; and said compressible filler material characterized as reducing its volume to become smaller in cross-section to lessen its peripheral surface in a pressurized condition whereby said compressible filler material peripheral surface in cross-section is less than said membrane peripheral surface cross-section so that said membrane becomes slack to permit conformal occupation of surface irregularities.

9. The invention as defined in claim 8 including:
strap means carried about said membrane for selectively applying pressure to said sealing membrane and said compressible filler material.

10. The invention as defined in claim 9 including:
a bleed orifice provided on said membrane openly communicating the interior of said membrane to atmosphere whereby applied pressure to said sealing means creates a slack condition of said membrane and a compressed condition of said compressible filler material.

* * * * *